United States Patent [19]

Mehra et al.

[11] 4,277,313

[45] Jul. 7, 1981

[54] RECOVERY OF 1,3-BUTADIENE

[75] Inventors: Yuv R. Mehra, Odessa; Ralph E. Clark, Corpus Christi, both of Tex.

[73] Assignee: El Paso Products Company, Odessa, Tex.

[21] Appl. No.: 134,687

[22] Filed: Mar. 27, 1980

[51] Int. Cl.³ .............................................. B01D 3/34
[52] U.S. Cl. ..................................... 203/32; 585/260; 585/261; 585/262
[58] Field of Search ............................... 585/259–262; 203/32, 28, 29

[56] References Cited

FOREIGN PATENT DOCUMENTS 983783 2/1965 United Kingdom ..................... 585/259

Primary Examiner—Frank Sever

[57] ABSTRACT

This invention provides a process for separating 1,3-butadiene from a $C_4$-hydrocarbon mixture which contains $C_4$-alkyne components.

In one embodiment, the invention involves a first step hydrogenation procedure for selectively hydrogenating the $C_4$-alkyne components, and a second step extractive distillation procedure for separating out a 1,3-butadiene rich selective solvent extract phase.

18 Claims, 1 Drawing Figure

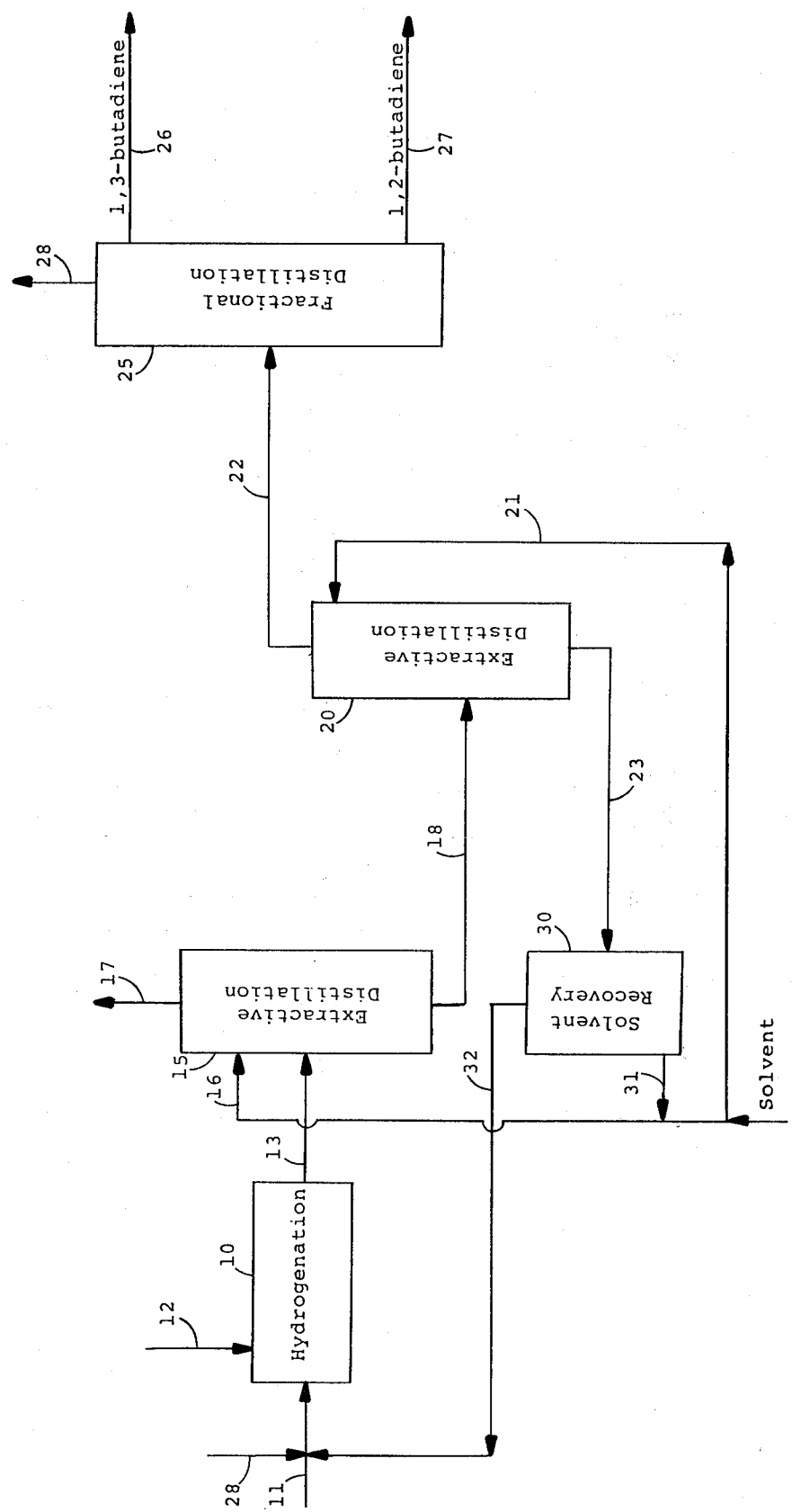

RECOVERY OF 1,3-BUTADIENE

BACKGROUND OF THE INVENTION

In the manufacture of ethylene and/or propylene by thermal cracking of a petroleum fraction such as liquified petroleum gas, naphtha or gas oil, substantial quantities of $C_4$-hydrocarbon mixtures are produced as co-products. These $C_4$-hydrocarbon streams contain significant percentages of 1,3-butadiene, 1,2-butadiene, butanes and butenes, as well as some highly reactive $C_4$-acetylenes (i.e., $C_4$-alkynes).

Recovery of 1,3-butadiene and other hydrocarbons in high purity from such $C_4$-hydrocarbon streams is well known. However, undesirable impurities such as $C_4$-acetylenes require special caution and equipment in recovering the desirable 1,3-butadiene and other hydrocarbons.

These undesirable $C_4$-acetylenes are particularly difficult to separate from 1,3-butadiene and other $C_4$-hydrocarbons contained in the $C_4$-hydrocarbon fraction by fractional distillation or other methods, and must be reduced to a level of parts per million to meet polymerization specifications for 1,3-butadiene or to avoid any subsequent formation of explosive metal acetylides in the process.

A diversity of methods have been developed in the prior art for the selective removal of $C_4$-acetylenes from $C_4$-hydrocarbon mixtures comprising butanes, butenes and 1,3-butadiene, with the ultimate objective of producing high purity 1,3-butadiene. The prior art methods include selective extraction procedures and selective hydrogenation procedures. In some cases a selective extraction procedure is employed in combination with a subsequent hydrogenation procedure, wherein most of the 1,3-butadiene content is removed before the said hydrogenation step.

U.S. Pat. No. 3,751,508 discloses a novel catalyst which is adapted for selective hydrogenation of acetylenic hydrocarbons in the concurrent presence of diolefinic hydrocarbons. The catalyst consists of a carrier containing at least 5 percent of magnesium-aluminum spinal ($MgAl_2O_4$), and an active component consisting of copper and nickel oxides.

U.S. Pat. No. 3,770,619 describes a two stage procedure for selectively hydrogenating an acetylenic type of impurity in a hydrocarbon mixture.

U.S. Pat. No. 3,842,137 describes a process for selective hydrogenation of $C_4$-acetylenes in admixture with 1,3-butadiene in the liquid phase which involves reacting the hydrocarbon admixture with a stream of hydrogen diluted to not more than 25 mole percent hydrogen in inert gas, in contact with a Group VIII noble metal supported catalyst.

U.S. Pat. No. 3,859,377 describes the selective hydrogenation of $C_4$-acetylenes in admixture with other $C_4$-hydrocarbons including 1,3-butadiene, by liquid phase hydrogenation with a hydrogen stream diluted to not more than 50 mole percent in inert gas, in the presence of a palladium on kieselguhr catalyst in which the kieselguhr has a pore volume which is substantially composed of macropores of greater than 700 Å.

Other U.S. Pat. Nos. which disclose methods for selective hydrogenation of $C_4$-acetylenes in the presence of 1,3-butadiene include 3,897,511; 3,898,298; 3,912,789; 4,101,451; and references cited therein.

U.S. Pat. No. 2,386,927 describes a process for selectively concentrating a conjugated diolefin from other close boiling more saturated hydrocarbons which involves extracting the hydrocarbon mixture with a dialkylamide type solvent to dissolve selectively the conjugated diolefin, and then recovering the diolefin from the solvent phase.

U.S. Pat. Nos. 3,436,436 and 3,436,438 are related references which are concerned with extractive distillation methods for selectively separating a $C_4$-diolefin from $C_4$-acetylenes and other $C_4$-hydrocarbons. Illustrative of one embodiment, U.S. Pat. No. 3,436,438 describes a process which involves subjecting the $C_4$-hydrocarbon mixture to extractive distillation with a dialkylamide type of solvent. The $C_4$-diolefin is separated as a distillate substantially free of $C_4$-acetylenes, and the $C_4$-acetylenes are dissolved in the liquid solvent extract phase. The extract phase subsequently is fractionated to separate the $C_4$-acetylenes from the solvent. In another embodiment, two extractive distillation stages are employed to yield butanes/butenes, $C_4$-diolefin, and $C_4$-acetylenes, respectively, as three separate fractions.

U.S. Pat. No. 4,049,742 describes a process for recovering 1,3-butadiene with the aid of a selective solvent from a $C_4$-hydrocarbon mixture containing hydrocarbons which are more soluble in said selective solvent than 1,3-butadiene (e.g., acetylenes), and hydrocarbons which are less soluble in said selective solvent than 1,3-butadiene. The $C_4$-hydrocarbon mixture is separated by the use of one or more extractive distillation zones, and the fraction containing the acetylenes and other solvent soluble hydrocarbons is subjected to catalytic hydrogenation.

The prior art methods developed for selectively recovering 1,3-butadiene from mixtures containing $C_4$-acetylenes and other $C_4$-hydrocarbons are generally effective for accomplishing the main objective. However, in terms of large scale plant operation, the prior art methods tend to have high overall capital requirements. They include special equipment and secondary processing procedures which are energy intensive.

It is an object of this invention to provide a process for recovery of high purity 1,3-butadiene from $C_4$-hydrocarbon mixtures, wherein the recovered 1,3-butadiene meets the specification requirements of polymerization processes.

It is another object of this invention to provide a process in which the concentration of $C_4$-acetylenes in 1,3-butadiene containing $C_4$-hydrocarbon mixtures is reduced in a first step, so as to minimize hazards and equipment fouling in subsequent process steps to recover high purity 1,3-butadiene.

Other objects and advantages of the present invention shall become apparent from the accompanying description and example.

DESCRIPTION OF THE INVENTION

One or more objects of the present invention are accomplished by the provision of a process for recovering 1,3-butadiene from a hydrocarbon mixture containing $C_4$-alkanes, $C_4$-alkenes, $C_4$-alkadienes and $C_4$-alkynes which comprises the steps of (1) selectively hydrogenating the alkynes in the hydrocarbon mixture; (2) contacting the hydrogenated hydrocarbon mixture in an extractive distillation zone with a selective solvent in which alkanes and alkenes are less soluble than 1,3-butadiene, and recovering from the said extractive distillation zone a distillate phase which contains alkanes and alkenes, and recovering from the said extractive distillation zone a solvent phase which contains dissolved 1,3-butadiene; and (3) separating the 1,3-butadiene from the solvent phase.

In another embodiment, this invention provides a process for recovering 1,3-butadiene from a hydrocarbon mixture containing butanes, butenes, 1,3-butadiene, methylacetylene, vinylacetylene and ethylacetylene which comprises the steps of (1) selectively hydrogenating the acetylenes in the hydrocarbon mixture with hydrogen in the presence of a hydrogenation catalyst; (2) introducing the hydrogenated hydrocarbon mixture into an intermediate zone of a first extractive distillation unit, and contacting the said hydrocarbon mixture with a selective solvent which flows downward in the extractive distillation unit and which solvent dissolves 1,3-butadiene more readily than the butanes and butenes; (3) recovering from the extractive distillation unit an overhead distillate fraction containing butanes and butenes, and recovering a bottom solution phase containing 1,3-butadiene; and (4) introducing the said solution phase into an intermediate zone of a second extractive distillation unit, and contacting the solution phase with additional selective solvent which flows downward in the second extractive distillation unit under conditions which provide for the recovery of an overhead distillate fraction containing 1,3-butadiene, and the recovery of a solvent phase which contains residual acetylenes.

For the purposes of the present invention, a typical $C_4$-hydrocarbon feedstock will contain components which include combinations of n-butane; isobutane; isobutene; butene-1; cis-butene-2; trans-butene-2; 1,2-butadiene; 1,3-butadiene; vinylacetylene; methylacetylene; ethylacetylene; pentanes; pentenes; and the like.

The 1,3-butadiene content of the $C_4$-hydrocarbon feedstock being processed normally will vary in the range between about 20–80 weight percent.

The $C_4$-alkyne content of a $C_4$-hydrocarbon feedstock normally will vary in the range between about 0.2–30 percent.

An important aspect of the present invention process embodiments is the first step selective hydrogenation of the $C_4$-alkyne content of the feedstream. Several advantages derive from this first stage procedure.

First, the removal of the $C_4$-alkynes in an early stage of the process eliminates the need for secondary processing steps to separate acetylenic components from diolefinic components, thereby saving considerable energy.

Second, the removal of the $C_4$-alkynes eliminates the need for special equipment for any subsequent safe processing of concentrated acetylenic byproduct fractions.

Third, the reduced $C_4$-alkynes content in the hydrogenated feedstream to the extractive distillation zone results in reduced maintenance expenses for cleaning of fouled distillation equipment.

Fourth, the reduced $C_4$-alkyne content in the hydrogenated feedstream to the extractive distillation zone results in reduced solvent losses in byproduct gases and polymerized materials.

Fifth, the hydrogenation step converts $C_4$-alkynes in the feedstream to the more valuable butene and butadiene derivatives, and improves the economics of the overall process.

The said first step hydrogenation reaction is conducted with a hydrogen source conventionally employed for hydrogenation reactions. The hydrogen may be employed undiluted, or diluted with an inert gas such as nitrogen. The hydrogen content of a diluted gas stream can vary over a broad range between about 10–90 volume percent, with the range between about 40–80 volume percent being preferred.

The hydrogenation may be accomplished either in the vapor phase or liquid phase, with the liquid phase being the preferred mode. If desired, an inert solvent can be employed as a hydrogenation medium. Suitable inert solvents include dimethylformamide, furfural, ethyl acetate, tetrahydrofuran, ethanol, butanol, cyclohexanol, and the like. It is particularly advantageous to employ the same inert solvent which is selected for the extractive distillation phase of the process (e.g., acetonitrile). The inert solvent can be employed in a quantity between about 5–50 weight percent of the hydrogenation medium.

The hydrogenation reaction is conducted isothermally at a temperature in the range between about 0°–150° C., and preferably at a temperature of about 10°–75° C. and a pressure in the range between about 30–300 psig.

The liquid hourly space velocity of the liquid medium through the hydrogenation zone catalyst bed can vary in the range between about 1–20, and normally will average in the range between about 5–10 v/v/hr.

The particular catalyst employed for the first step hydrogenation reaction is preferably one of the various prior art catalysts which are known to be selective for hydrogenation of $C_4$-alkynes in the presence of conjugated diolefins. A typical catalyst is a supported composition which contains a Group VIII metal of the Periodic Table, such as cobalt, nickel, palladium, platinum, and the like. Suitable supports include charcoal, silica, alumina, diatomaceous earth, calcium carbonate, and mixtures thereof.

The metal content of the catalyst can vary in the range between about 0.1–5 weight percent. In some cases it is advantageous to use a mixture of metals in the catalyst, such as a combination of Group VIII and Group II(b) metals, so as to achieve improved hydrogenation reactivity and selectivity.

When the first step hydrogenation reaction is conducted continuously, the activity of the catalyst tends to exhibit reduced activity and selectivity. The catalyst can be reactivated by subjecting it to a regeneration procedure. A typical regeneration procedure involves stripping with concentrated hydrogen, washing with a polar solvent, treating with hydrogen, and calcining in air diluted with nitrogen or steam, as described in U.S. Pat. Nos. 3,859,377 and 3,912,789.

After the first step hydrogenation reaction is completed, the hydrogenated hydrocarbon effluent from the hydrogenation unit is entered into the second step extractive distillation unit.

A selective solvent is employed in which butanes and butenes are less soluble than 1,3-butadiene, and in which $C_4$-alkynes are more soluble than 1,3-butadiene. Suitable solvents include dimethylformamide, diethylformamide, dimethylacetamide, formylmorpholine, acetonitrile, furfural, butyrolactone, N-methylpyrrolidone, and the like. Dimethylformamide is an excellent selective solvent for the purposes of the present invention. The quantity of solvent is a function of the amount of butadiene in the feed and can vary between about 0.5–20 volumes per volume of liquid hydrocarbon feedstream in the extractive distillation unit.

The temperature, pressure, reflux ratio and other processing variables are balanced so as to achieve the desired selective separation of hydrocarbon components on the basis of degree of solubility in the selective solvent. The hydrocarbon feedstream is introduced into an intermediate zone of an extractive distillation unit which preferably has the equivalent of at least 70 plates.

The selective solvent (e.g., dimethylformamide) is introduced into an upper zone of the extractive distillation unit, and flows downward in countercurrent contact with the ascending vapors.

The result of the extractive distillation procedure is the provision of an overhead distillate fraction which is rich in butanes and butenes, and the provision of a bottom liquid extract phase which consists of the solvent and dissolved hydrocarbon components such as 1,3-butadiene and $C_4$-alkynes.

In a single stage extractive distillation embodiment, the said bottom liquid extract phase is transferred to a solvent stripping unit, where a 1,3-butadiene rich fraction is separated, and the solvent is recovered for recycle.

In a two stage extractive distillation embodiment, the said bottom liquid extract phase is entered into a second extractive distillation unit. This unit operates in a similar manner to the first unit, except that the processing conditions are balanced to provide an overhead distillate fraction which is rich in 1,3-butadiene, and a bottom liquid extract phase which consists of the solvent and dissolved hydrocarbon components such as residual $C_4$-alkynes and other compounds which are more soluble in the solvent than 1,3-butadiene.

The overhead distillate fraction from the said second extractive distillation unit is subjected to fractional distillation to yield high purity 1,3-butadiene as a major component, and 1,2-butadiene as a minor component.

The bottom liquid extract from the said second extractive distillation unit is transferred to a solvent stripping unit, where a hydrocarbon fraction containing residual $C_4$-alkynes and 1,3-butadiene is separated from the solvent phase. The said hydrocarbon fraction is suitable for recycle to the hydrogenation step of the invention process. Optionally, the said hydrocarbon fraction can be hydrogenated in a separate hydrogenation unit, and recycled directly to the first extractive distillation unit.

The following example is further illustrative of the present invention. The reactants and other specific ingredients are presented as being typical, and various modifications can be derived in view of the foregoing disclosure within the scope of the invention.

EXAMPLE

The practice of the present invention as a continuous process can be better understood by reference to the drawing which is illustrated as a flow diagram.

As illustrated in the drawing, a hydrocarbon feedstock is charged continuously into hydrogenation unit 10 through line 11. The feedstock contains about 47 weight percent 1,3-butadiene, 0.3 weight percent 1,2-butadiene, 1.6 weight percent vinylacetylene, 0.5 weight percent methylacetylene, 0.7 weight percent ethylacetylene, and the remainder consists of butanes and butenes, and some minor quantities of $C_5$-hydrocarbons.

A gas stream (40 percent hydrogen/60 percent nitrogen) is fed into Hydrogenation unit 10 through line 12.

The Hydrogenation unit 10 contains a bed of hydrogenation catalyst pellets consisting of about 0.7 weight percent palladium on alumina.

The hydrogenation reaction is conducted in the liquid phase at a temperature of about 30° C. and a pressure of about 85 psig and at a liquid hourly space velocity of about 10.

A hydrogenated hydrocarbon effluent is withdrawn from Hydrogenation unit 10 and introduced through line 13 into an intermediate zone of Extractive Distillation unit 15. Dimethylformamide solvent in appropriate amounts is entered through line 16 into an upper zone of Extractive Distillation unit 15, and the solvent passes downward in countercurrent contact with the hydrocarbon mixture. Extractive Distillation unit 15 has at least 70 plates. The dimethylformamide is fed at the rate of about 6-8 volumes per volume of $C_4$-hydrocarbons.

The bottom temperature in Extractive Distillation unit 15 is about 150° C. and the operating pressure is about 70 psig. The unit is operated with an appropriate rate of reflux to achieve efficient selective extraction and distillation of the hydrocarbon components.

A distillate fraction is recovered overhead from Extractive Distillation unit 15 via line 17. The distillate fraction, comprised substantially of butanes and butenes, is removed from the operating system.

A bottom solution consisting of dimethylformamide and solute components is withdrawn from Extractive Distillation unit 15 through line 18 and fed continuously into an intermediate zone of Extractive Distillation unit 20. This unit is operated with a bottom temperature of about 160° C. and a pressure of about 5.0 psig. Dimethylformamide is fed into Extractive Distillation unit 20 through line 21 at a rate of about 6-8 volumes per volume of hydrocarbon fed through line 18 into Extractive Distillation unit 20.

A distillate fraction consisting substantially of butadienes is withdrawn continuously from Extractive Distillation unit 20 and fed through line 22 into Fractional Distillation unit 25. 1,3-Butadiene and 1,2-butadiene are removed from Fractional Distillation Unit 25 through lines 26 and 27, respectively. An overhead fraction, containing light end components such as methylacetylene, is withdrawn through line 28. This fraction is recycled to Hydrogenation unit 10.

A bottom liquid dimethylformamide phase containing solute components is withdrawn from Extractive Distillation unit 20 through line 23 and fed into Solvent Recovery unit 30.

Dimethylformamide is recovered from Solvent Recovery unit 30 through line 31 and recycled to Extractive Distillation units 15 and 20.

An overhead hydrocarbon fraction is withdrawn from Solvent Recovery unit 30 through line 32, and recycled to Hydrogenation unit 10. This hydrocarbon fraction consists substantially of residual vinylacetylene and ethylacetylene, and contains small quantities of 1,3-butadiene and 1,2-butadiene.

What is claimed is:

1. In a process for recovering 1,3-butadiene from a hydrocarbon mixture containing $C_4$-alkanes, $C_4$-alkenes, $C_4$-alkadienes and $C_4$-alkynes the improvement which comprises (1) providing a crude hydrocarbon mixture containing $C_4$-alkanes, $C_4$-alkenes, $C_4$-alkadienes and between about 0.2-30 percent $C_4$ alkynes; (2) directly introducing said crude mixture into a hydrogenation zone and selectively hydrogenating the alkynes in the mixture whereby the alkyne content of the mixture is substantially reduced thereby eliminating the need for secondary processing steps to separate alkyne components from alkadienes components; (3) contacting the hydrogenated hydrocarbon mixture in an extractive distillation zone with a selective solvent in which alkanes and alkenes are less soluble than 1,3-butadiene, and recovering from the said extractive distillation zone a distillate phase which contains alkanes and alkenes, and recovering from the said extractive distillation zone a solvent phase which contains dissolved 1,3-butadiene; and (4) separating the 1,3-butadiene from the solvent phase.

2. A process in accordance with claim 1 wherein the 1,3-butadiene content of the hydrocarbon feed is in the range between about 20–80 weight percent.

3. A process in accordance with claim 1 wherein the hydrogenation in step (2) is conducted in the presence of hydrogen and a hydrogenation catalyst.

4. A process in accordance with claim 1 wherein the hydrogenation reaction in step (2) is conducted in liquid phase at a temperature in the range between about 10°–75° C. in the presence of hydrogen and a hydrogenation catalyst.

5. A process in accordance with claim 1 wherein the hydrogenation reaction in step (2) is conducted in gas phase at a temperature in the range between about 100°–150° C. in the presence of hydrogen and a hydrogenation catalyst.

6. A process in accordance with claim 1 wherein the selective solvent in step (3) is dimethylformamide.

7. A process in accordance with claim 1 wherein the selective solvent in step (3) is selected from the group consisting of N-methylpyrrolidone, furfural, acetonitrile and diethylformamide.

8. A process in accordance with claim 1 wherein the solvent phase recovered in step (4) is recycled to step (3).

9. In a process for recovering 1,3-butadiene from a hydrocarbon mixture containing $C_4$-alkanes, $C_4$-alkenes, $C_4$-alkadienes and $C_4$-alkynes the improvement which comprises (1) providing a crude hydrocarbon mixture containing butanes, butenes, 1,3-butadiene, 1,2-butadiene pentanes, pentenes and between about 0.2–30 percent of $C_4$-alkynes comprising methylacetylene, vinylacetylene and ethylacetylene; (2) directly introducing said crude mixture into a hydrogenation zone and selectively hydrogenating the alkynes in the mixture whereby the alkyne content of the mixture is substantially reduced, thereby eliminating the need for secondary processing steps to separate alkyne components from butadiene components; (3) introducing the hydrogenated hydrocarbon mixture into an intermediate zone of a first extractive distillation unit, and contacting the said hydrocarbon mixture with a selective solvent in the extractive distillation unit and which solvent dissolves 1,3-butadiene more readily than the butanes and butenes; (4) recovering from the extractive distillation unit an overhead distillate fraction containing butanes and butenes, and recovering a bottom solution phase containing 1,3-butadiene; and (5) introducing the said solution phase into an intermediate zone of a second extractive distillation unit, and contacting the solution phase with additional selective solvent in the second extractive distillation unit under conditions which provide for the recovery of an overhead distillate fraction containing 1,3-butadiene, and the recovery of a solvent phase which contains residual acetylenes.

10. A process in accordance with claim 9 wherein the hydrogenation reaction in step (2) is conducted in the liquid phase at a temperature in the range between about 10°–75° C.

11. A process in accordance with claim 10 wherein the hydrogenation catalyst in step (2) contains a Group VIII metal.

12. A process in accordance with claim 10 wherein the selective solvent in step (3) and step (5) is dimethylformamide.

13. A process in accordance with claim 10 wherein the selective solvent in step (3) and step (5) is selected from the group consisting of N-methylpyrrolidone, furfural, acetonitrile and diethylformamide.

14. A process in accordance with claim 10 wherein the solvent phase recovered in step (5) is fractionated to provide a solvent fraction for recycle to step (3) and (5), and a hydrocarbon fraction containing acetylenes for recycle to step (2).

15. A process in accordance with claim 10 wherein the overhead distillation fraction containing 1,3-butadiene is subjected to fractional distillation into a stream of methyl acetylene which is recycled to step (2), a stream of high purity 1,3-butadiene and a stream of 1,2-butadiene and heavier components in the hydrocarbon mixture.

16. A process in accordance with claim 10 wherein the hydrogenation reaction in step (2) is conducted in gas phase at a temperature in the range between about 100°–150° C. in the presence of hydrogen and a hydrogenation catalyst.

17. A process in accordance with claim 10 wherein the operating pressure of the second extractive distillation unit in step (5) is between 0 to 65 psig.

18. A process in accordance with claim 10 wherein the solvent phase recovered in step (5) is fractionated to provide a solvent fraction for recycle to step (3) and (5), and a hydrocarbon fraction containing acetylenes for a separate hydrogenation step and then recycle to step (3).

* * * * *

UNITED STATES PATENT OFFICE
CERTIFICATE OF CORRECTION

Patent No. 4,277,313            Dated July 7, 1981

Inventor(s) Yuv R. Mehra and Ralph E. Clark

It is certified that error appears in the above-identified patent and that said Letters Patent are hereby corrected as shown below:

In Claims 11 through 18, line 1 of each, the number "10" should read -- 9 --.

Signed and Sealed this

Twenty-fourth Day of November 1981

[SEAL]

*Attest:*

*Attesting Officer*

GERALD J. MOSSINGHOFF

*Commissioner of Patents and Trademarks*